(12) United States Patent
Hudson

(10) Patent No.: US 6,599,472 B1
(45) Date of Patent: Jul. 29, 2003

(54) OIL SOLUBLE SCAVENGERS FOR SULFIDES AND MERCAPTANS

(75) Inventor: Alice P. Hudson, Jupiter, FL (US)

(73) Assignee: Surface Chemists of Florida Inc., Jupiter, FL (US)

( * ) Notice: Subject to any disclaimer, the term of this patent is extended or adjusted under 35 U.S.C. 154(b) by 0 days.

(21) Appl. No.: 09/704,478

(22) Filed: Nov. 3, 2000

(51) Int. Cl.$^7$ ............... A61L 9/00; A62B 7/08
(52) U.S. Cl. ............... 422/5; 422/1; 422/28; 422/34; 422/120
(58) Field of Search ............... 422/1, 5, 28–32, 422/34–37, 120, 123

(56) References Cited

U.S. PATENT DOCUMENTS

| | | | |
|---|---|---|---|
| 2,584,041 A | * | 1/1952 | Lowak |
| 4,902,408 A | * | 2/1990 | Reichert et al. |
| 5,443,698 A | * | 8/1995 | Mahoney et al. |
| 6,077,794 A | * | 6/2000 | Tabata et al. |
| 6,106,853 A | * | 8/2000 | Cox et al. |

\* cited by examiner

*Primary Examiner*—Robert J. Warden, Sr.
*Assistant Examiner*—Monzer R. Chorbaji

(57) ABSTRACT

This invention provides oil soluble sulfhydryl compound scavengers which are salt compositions of the formula:

$$M^{n+}(R\text{—}CO_2^-)_x(OH)_{n-x}$$

wherein M is a metal ion whose sulfide salt is less than 0.1% soluble in water, n is 2 or 3, x is an integer from 1 to n, and R a hydrocarbyl radical containing from about 4 to about 19 carbon atoms, or mixture of these compositions.

A method is also provided to control odors produced by sulfhydryl compounds wherein the he said sulfhydryl compounds are contacted with the metal salts described above.

13 Claims, No Drawings

OIL SOLUBLE SCAVENGERS FOR SULFIDES AND MERCAPTANS

FIELD OF THE INVENTION

This invention relates to chemical compositions which are metal salts of carboxylic acids herein described, that are soluble in hydrocarbon oils and are used to inactivate odor producing sulfhydryl compounds that are present in hydrocarbon oils or other organic materials, in mixtures containing these materials, and in compositions which come in contact with these materials.

BACKGROUND OF THE INVENTION

The presence of sulfhydryl compounds and particularly hydrogen sulfide in hydrocarbon oils and other organic materials, mixtures containing these materials, and aqueous, solid, or gaseous phases in contact with these materials is an important environmental and safety and health problem in a broad range of industries. Sulfhydryl compounds include $H_2S$, organo sulfur compounds containing S—H groups also called mercaptans, thiol carboxylic acids RC(O)SH, dithio acids RC(S)SH, and related compounds.

In the petroleum industry the $H_2S$ content of crude oils in many areas of the world is high enough to present environmental and safety hazards. Hydrogen sulfide is flammable, corrosive, highly toxic, and a strong irritant. It is produced by sulfate reducing bacteria in the anaerobic environments encountered in oil wells and is highly soluble in the crude oil, from which it is released when the oil is removed from the well. $H_2S$ may be transferred to oil based drilling fluids when the fluids come in contact with $H_2S$ rich environments, where it becomes a hazard as the drilling fluid is recirculated from the well to the surface.

Sulfhydryl compounds and their resultant odors are also a problem in metal working environments. Sulfate reducing bacteria are often present in the recirculating metal working fluid systems, and though the bacteria can usually be controlled by the use of biocidal compositions, these biocide systems are difficult to control and monitor, and can occasionally fail, resulting in the offensive and hazardous formation of $H_2S$ in the fluids. The biocides cannot remove $H_2S$ after it has formed and thus a back-up means for removing it is desirable. Also, sulfurized oils are widely used in this industry because the sulfur from these compositions reacts with iron and provides lubricating benefits. These oils release undesirable volatile hydrogen sulfide and mercaptan compounds which are not essential to the effectiveness of the lubricants, and it would be desirable to control odors from these compounds.

Sulfhydryl compounds and particularly $H_2S$ can present environmental and toxicity problems in gaseous phases in confined spaces, as for instance in sewage treatment facilities and particularly in shipping and storage containers for moisture sensitive materials that may emit $H_2S$. It would be desirable to have a scavenger that could reduce the $H_2S$ concentrations in such locations. It would be particularly advantageous to have such a scavenger that is active in the absence of an aqueous phase.

A number of methods have been proposed to control hydrogen sulfide odors in hydrocarbon containing systems.

WO 98/02501 describes bisoxazolidines prepared by the reaction of 1, 2 or 1, 3 amino alcohols containing 3 to 7 carbon atoms with aldehydes containing 4 or fewer carbon atoms. These products can be made oil soluble by the correct choice of starting materials, and react with sulfhydryl compounds present in oil and gas streams to neutralize them. U.S. Pat. No. 5,347,004 describes reaction products of alkoxyalkylene amine, ammonia, and dialkylamines with aldehydes. These products are used to remove hydrogen sulfide from gas streams which are sparged into water solutions of the products. U.S. Pat. No. 6,024,866 describes reaction products of an alkylenepolyamine with formaldehyde which can be made either water or hydrocarbon soluble.

Zinc and iron compounds have been used for this application. U.S. Pat. No. 3,928,211 describes the use of inorganic zinc salts preferably dispersed into aqueous or non-aqueous oil well drilling fluids with an organic dispersant such as lignin containing materials. U.S. Pat. No. 4,147,212 describes a water soluble zinc ammonium carbonate complex used to remove hydrogen sulfide from oils and gases by contact with aqueous solutions of the complex. U.S. Pat. No. 5,792,438 describes the activation of iron oxide by copper oxide to increase the rate of reaction of iron oxide and sulfur compounds. U.S. Pat. No. 4,756,836 discloses the use of chelated iron to oxidize $H_2S$ to elemental sulfur. The iron chelate is oxygen regenerated and recycled.

Metal salts of carboxylic acids and methods for their production are known. U.S. Pat. No. 2,584,041 describes a method to produce oil soluble metal salts of carboxylic acids in organic solvents by a hydrous two-phase fusion process. U.S. Pat. No. 2,890,232 describes a method for preparing polyvalent metal soaps of higher aliphatic monocarboxylic acids by a slurry process in which the acids are heated and slurried with the metal oxides in the presence of water. U.S. Pat. No. 5,443,698 describes an electrolytic method for synthesizing metal carboxylates.

It is an object of this invention to provide compositions which effectively remove odors caused by sulfhydryl compounds from crude oils, metal working fluids, and other organic materials; and liquid, solid or gaseous phases in contact with these materials.

It is a further object to provide compositions which are readily soluble in the hydrocarbon oils encountered in environments such as oil wells and metal working fluids.

It is a further object to provide compositions which do not contain aldehydes or toxic metals.

It is a further object to provide a method for the removal of odor producing sulfhydryl compounds from crude oils, metal working fluids, and other organic materials; and liquid, solid or gaseous phases in contact with these materials.

BRIEF DESCRIPTION OF THE INVENTION

The oil soluble sulfhydryl compound scavengers of this invention are metal carboxylates or soaps of the formula:

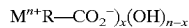

$$M^{n+}R\text{—}CO_2^-)_x(OH)_{n-x}$$

wherein M is a metal ion whose sulfide salt is less than 0.01% soluble in water, n is 2 or 3, x is an integer from 1 to n, and R a hydrocarbyl radical containing from about 4 to about 19 carbon atoms, and mixtures of these compositions.

A method is also provided to control odors produced by sulfhydryl compounds wherein the compositions containing the said sulfhydryl compounds are contacted with the metal carboxylates described above.

DESCRIPTION OF THE PREFERRED EMBODIMENTS

The metal carboxylate salts of this invention can be prepared by known methods starting from carboxylic acids or their water soluble salts, and metals, metal oxides or metal salts.

The carboxylic acids used to prepare the compositions of this invention contain from about 5 to about 20 carbon atoms, and are chosen from those which form oil soluble salts with the metal ions of this invention. Preferred are acids which form metal salts that are liquid below about 100° C., and most preferred are those which form metal salts that have pour points below about 25° C. As a rule the formation of low melting salts requires that the carboxylic acids used in the synthesis have highly branched structures. Also preferred are lower molecular weight acids because they are more efficient on a weight basis for the intended application. Examples of Suitable Acids Include:

1. Neoacids. These are synthesized by reacting under high pressure and at elevated temperature a branched olefin and high-purity carbon monoxide in the presence of an acidic catalyst and water. The resulting acids have a tertiary carbon adjacent to the carboxyl group and are mixtures of isomers of the structure:

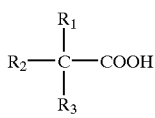

wherein $R_1$, $R_2$, and $R_3$ are each alkyl radicals containing 1 to about 16 carbon atoms, with the total number of carbon atoms contained in $R_1$, $R_2$, and $R_3$ being from about 3 to about 18.

Neoacids with 7 or more carbon atoms are mixtures of isomers. For example, the typical isomer distribution of neodecanoic acid is: $R_1$ and $R_2$ are methyl, $R_3$ is $C_6$, 31%; $R_1$ is methyl, $R_2$ and $R_3$ are $C_2$ to $C_5$, 67%; $R_1$ is $C_2$, $R_2$ and $R_3$ are $C_2$ or $C_3$, 2%.

Readily available and suitable neoacids include neopentanoic acid, neoheptanoic acid, neooctanoic acid, neononanoic acid, neodecanoic acid, and neotridecanoic acid. Neoacids with up to an average of about 20 carbon atoms are also available as mixtures of chain lengths and isomers, and are also suitable, as are mixtures of any of the described neoacids in any proportions. Neodecanoic acid is readily available and forms low viscosity salts and is preferred.

2. Naphthenic acids. As used herein, this term means the generic designation of monocarboxylic acids of naphthene hydrocarbons, present in crude mineral oils, which acids have the formula $R_4(CH_2)_n COOH$, wherein $R_4$ is a cyclic nucleus composed of one or more rings, i.e., cyclohexane, cyclopentane, and their alkylated cyclic nuclei in general; and n is an integer from 1 to about 14. The carboxylic acid group combines with the ring nucleus ($R_4$) through methylene (—$CH_2$—)$_n$ groups. The simplest and typical acid, when n=1 is cyclopentane acetic acid.

Commercial naphthenic acids suitable in this invention are mixtures of inseparable organic acids having from 7 to about 20 carbon atoms and a cyclic nucleus. Accordingly, the naphthenic acid is used as a mixture of substances having the formula given above, and may also contain a minor amount of upsaponifiable material, which is unspecified but usually hydrocarbon in nature. Preferred naphthenic acids have equivalent weights per carboxylic acid functionality of less than about 300, and more preferred naphthenic acids less than about 250.

3. Isoacids of the structure:

$$R_5—CH_2—COOH$$

wherein $R_5$ is a hydrocarbyl group containing from about 3 to about 17 carbon atoms including at least one substituted methyl group on other than the terminal carbon atom. Commercially available isoacids are usually mixtures of isomers which differ in the number and position of the methyl substitutions. Suitable available isoacids include isopentanoic acid, isoheptanoic acid, isooctanoic acid, isononanoic acid, isodecanoic acid, and isotridecanoic acid.

4. Guerbet acids, obtained from Guerbet alcohols, of the structure:

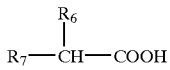

wherein $R_6$ is a hydrocarbyl group containing from about 2 to about 8 carbon atoms, and $R_7$ is a hydrocarbyl group containing from about 4 to about 10 carbon atoms, and $R_6$ always contains exactly 2 carbon atoms less than $R_7$. Available and suitable Guerbet acids include 2-ethylhexanoic acid, 2-butyloctanoic acid, 2-hexyldecanoic acid, and 2-octyldodecanoic acid.

5. Unsaturated acids such as oleic acid, and tall oil fatty acid.

Saturated straight chain fatty acids are less preferred because the metal salts of these acids usually have melting points above 100° C. Zinc laurate melts at 128° C and zinc stearate melts at 130° C.

The metal ions used to prepare the carboxylate salts of this invention are chosen from those which form water insoluble or sparingly soluble sulfide salts. Preferably the metal sulfides have solubility in water less than 0.01 g/100 cm³. The metal sulfides shown in the following table all are adequately insoluble. The preferred metals have low toxicity in the environment; thus highly toxic metals such as Hg, Pb, and Cd are less preferred. Because these compositions may in some applications be in contact with aqueous phases and at the same time with equipment such as drilling casings constructed of iron is it also preferred that the metals be more electronegative than iron so that they do not electrodeposit on the iron surfaces and cause corrosion of the iron. Because they are relatively nontoxic in the environment and do not cause iron corrosion, Zn, Fe, and Mn are the preferred metal ions. The Zn salts are readily synsthesized, are low in color, and are usually less viscous than other salts, and are most preferred.

| Metal | S salt | Solubility, g/100 cm³ | Standard Electrode Potential vs. H | |
|-------|--------|-----------------------|-----------|---------|
| Ag | Ag₂S | 8.4 × 10⁻¹⁵ | $Ag^+ + e^- \rightarrow Ag$ | +0.799 |
| Hg | HgS | insoluble | $Hg^+ + e^- \rightarrow Hg$ | +0.789 |
| Cu | CuS | 0.000033 | $Cu^{2+} + 2e^- \rightarrow Cu$ | +0.337 |
| Pb | PbS | 0.000086 | $Pb^{2+} + 2e^- \rightarrow Pb$ | −0.126 |
| Sn | SnS₂ | 0.0002 | $Sn^{+2} + 2e^- \rightarrow Sn$ | −0.136 |
| Ni | NiS | 0.00036 | $Ni^{+2} + 2e^- \rightarrow Ni$ | −0.250 |
| Co | CoS | 0.00038 | $Co^{+2} + 2e^- \rightarrow Co$ | −0.280 |
| Cd | CdS | 0.00013 | $Cd^{+2} + 2e^- \rightarrow Cd$ | −0.403 |
| Fe | FeS | 0.00062 | $Fe^{+2} + 2e^- \rightarrow Fe$ | −0.440 |
| Zn | ZnS | 0.00069 | $Zn^{+2} + 2e^- \rightarrow Zn$ | −0.763 |
| Mn | MnS | 0.00047 | $Mn^{+2} + 2e^- \rightarrow Mn$ | −1.185 |

The metal carboxylates of this invention are soluble in hydrocarbon oils. For the purposes of this invention hydrocarbon oils are described as compositions which are substantially free of elements other than carbon and hydrogen, and have flash points greater than about 90° C. measured by the Tagg Closed Cup method. They may contain unsaturation, aromatic groups, and branched and cyclic structures.

The oil soluble metal carboxylates are in general known compositions and can be synthesized by methods described in the art. Suitable methods include:

1. Reaction of the metal oxide or hydroxide with the carboxylic acid. This method is described in U.S. Pat. No. 2,890,232, which is incorporated herein by reference. We have found that reactions of ZnO with the carboxylic acids of this invention do not require the addition of excess water to obtain an adequately fast reaction, if the reaction mix is heated at a rate such that the water released in the reaction is not driven off before the reaction is completed. An excess of ZnO beyond the amount necessary to exactly neutralize the carboxylic acid can be added up to about a two fold excess.

2. Double decomposition reactions using water soluble metal salts and water soluble carboxylate salts. In this method water solutions of the reactants are mixed and the oil soluble salt separates from a water solution of the salt of the counterions. This method usually requires the addition of a solvent to decrease the viscosity of the oil soluble salt, and the aqueous salt solution byproduct may create a disposal problem.

3. Direct reaction of the carboxylic acid and the metal in the presence of water. This method is described in U.S. Pat. No. 2,584,041, incorporated herein by reference. This method requires the addition of solvent and water, and the reaction proceeds rather slowly.

This invention also encompasses a method for controlling odors produced by sulfhydryl compounds wherein the compositions containing the said sulfhydryl compounds are contacted with the metal salts of this invention.

For applications in which the odor producing sulfhydryl compounds are dissolved in hydrocarbon or other organic materials, such as $H_2S$ containing crude oils, nonaqueous metal working fluids, and the like, the metal carboxylate scavenger compounds of this invention can be added directly to the materials. It may be desirable to dilute the metal carboxylates with a diluant to decrease the viscosity and allow for more efficient mixing of the scavenger throughout the odorous material. Suitable diluants are low viscosity organic solvents and oils that are compatible with both the scavenger and the substrate. Low viscosity mineral oils are highly suitable. The application level required is at least enough to react with the sulfhydryl materials present. When zinc neodecanoate is used to remove $H_2S$, approximately 12.5 parts by weight of scavenger is required for each part of $H_2S$ present.

For applications in water based metal working fluids, the metal carboxylate scavenger compositions of this invention can be added directly to aqueous system with good agitation. Preferably they can be dispersed or dissolved into a portion of the base fluid, which typically comprises a sulfated hydrocarbon material, and then added to the water based fluid.

For removing odors caused by sulfhydryl compounds from gaseous phases, the scavenger compositions of this invention can be contacted with the gaseous materials by a number of means. The effectiveness of the compositions will depend on the surface area of the scavenger composition in contact with the gaseous phase. In some applications, the scavengers can be sprayed, either by themselves or dissolved in an oil or solvent, or emulsified into water, as fine particle droplets into the contaminated volume. In other applications, particularly in closed spaces, the scavenger compositions can be mixed with a high surface area powder such as precipitated silica, diatomaceous earth, and the like, to form a powdered composition which can be exposed to the atmosphere in the closed space. In other applications the scavenger compositions can be distributed onto the fibers of highly absorbent low density fiber mats, which are then exposed to the contaminated gaseous compostions.

The following examples further illustrate the invention. As used herein all parts or percentages are by weight unless otherwise indicated.

EXAMPLE 1

Zinc neodecanoate was prepared as follows: 172 g (1 mole) of neodecanoic acid was warmed to 70° C. and 40.7 g (0.5 moles) of ZnO was added with stirring over 10 minutes. When the addition was completed the mixture was heated to 110° C. and held at 110 to 120° C. for about one hour while continuing to stir. The reaction proceeded to form a clear solution with the loss of 9 g of water. The product was a clear viscous liquid with a viscosity of 6000 centipoise (cps) at 25° C.

EXAMPLE 2

The procedure of Example 1 was followed and zinc neodecanoate was prepared containing (a) 0.55 moles (44.8 g), (b) 0.60 moles (48.8 g) and (c) 0.65 moles (52.9 g) of ZnO per mole of neodecanoic acid. The resulting products were clear viscous liquids with viscosities of (a) 7200 cps, (b) 13,000 cps and (c) 22,000 cps.

The following zinc salts were prepared by the procedure of Example 1:

EXAMPLE 3

87.6 g of tall oil fatty acid was reacted with 12.4 g of ZnO. The product was a solid which melted at 70° C.

EXAMPLE 4

78 g of 2-ethyl hexanoic acid was reacted with 22 g of ZnO. The product was a viscous liquid, with viscosity>200,000 cps at 25° C.

EXAMPLE 5

79.5 g of isononanoic acid was reacted with 20.5 g of ZnO. The product was a solid, mp. 95° C.

EXAMPLE 6

71.5 g of isopentanoic acid was reacted with 28.5 g of ZnO. The product was a solid, mp. 60° C.

EXAMPLE 7

84 g of isotricanoic acid was reacted with 16 g of ZnO. The product is a viscous liquid with viscosity>200,000 cps at 25° C.

EXAMPLE 8

86.9 g of naphthenic acid with an equivalent weight of 269 was reacted with 13.1 g of ZnO. The product was a viscous liquid with viscosity>200,000 cps at 25° C. On dilution with 1 part of 100 sec paraffinic oil to 3 parts of zinc naphthenate, the viscosity was 35,000 cps, and when diluted 1:1 with the oil, the viscosity was 4000 cps.

EXAMPLE 9

84.6 g of naphthenic acid with an equivalent weight of 224 was reacted with 15.4 g of ZnO. The product was a viscous liquid with viscosity>200,000 cps at 25° C. On dilution with 1 part of 100 sec paraffinic oil to 3 parts of zinc naphthenate, the viscosity was 17,000 cps, and when diluted 1:1 with the oil, the viscosity was 2000 cps.

EXAMPLE 10

82.8 g of naphthenic acid with an equivalent weight of 196 was reacted with 17.2 g of ZnO. The product was a viscous liquid with viscosity>200,000 cps at 25° C. On dilution with 1 part of 100 sec paraffinic oil to 3 parts of zinc naphthenate, the viscosity was 14,000 cps, and when diluted 1:1 with the oil, the viscosity was 1500 cps.

EXAMPLE 11

78 g of neooctanoic acid was reacted with 22 g of ZnO. The product was a solid with a melting point of 95° C.

EXAMPLE 12

88.2 g of a mixture of $C_9$ to $C_{28}$ neoacids with an equivalent weight for the mixture of 302 was reacted with 12.8 g of ZnO. The product is a viscous liquid with a viscosity of 11,500 cps at 25° C.

EXAMPLE 13

Copper neodecanoate was prepared by the following procedure: 12.5 g (0.05 moles) of $CuSO_4.5H_2O$ was dissolved in 50 g of water. 50 ml of toluene was added, and with vigorous stirring 77.6 g of a 25% solution of sodium neodecanoate (0.1 moles) was added in about 20 minutes. Rapid stirring was continued for 10 minutes after the addition was complete, stirring was discontinued, and the mixture was allowed to stand overnight to separate to a deep blue-green organic phase and a clear colorless water phase. The organic phase weighed 101 g and contained 18.2% copper neodecanoate, which after removing the solvent by evaporation was a blue green viscous liquid with viscosity>200,000 cps.

EXAMPLE 14

Nickel neodecanoate was prepared by the following procedure: 3.74 g (0.05 moles) of NiO was added to 25 g (0.1 moles) of 15% HCl. 50 ml of toluene was added, and with vigorous stirring 77.6 g of a 25% solution of sodium neodecanoate (0.1 moles) was added in about 20 minutes. Rapid stirring was continued for 10 minutes after the addition was complete, stirring was discontinued, and the mixture was allowed to stand overnight to separate. After standing a clear green organic phase separated from an emulsion water phase. The organic phase was separated and the water emulsion was washed with 3×25 ml portions of toluene, until the water phase was clear and colorless. The toluene washes were combined with the organic layer to produce 96 g of a toluene phase containing 18.2% nickel neodecanoate. On removing the toluene by evaporation the nickel neodecanoate was a green viscous liquid with viscosity>200,000 cps.

EXAMPLE 15

Iron neodecanoate was prepared by a procedure based on U.S. Pat. No. 2,584,041 Example 14. 86 g (0.5 moles) of neodecanoic acid, 125 g of xylene, 25 g of water, and 12.7 g of iron powder (100 mesh) were charged to a 500 ml round bottom flask equipped with a stirrer, condenser, air inlet tube, and heating. The mixture was heated to reflux and refluxed for 7 hours, cooled and the organic phase separated from the water phase and unreacted Fe. The organic phase contained 65.2 g iron neodecanoate which on removal of the xylene by evaporation was a dark amber viscous liquid, with viscosity 10,000 cps.

EXAMPLE 16

Manganese neodecanoate was prepared by the following procedure: 8.45 g (0.05 moles) of $MnSO_4.H_2O$ was dissolved in 50 g of water. 50 ml of toluene was added, and with vigorous stirring 77.6 g of a 25% solution of sodium neodecanoate (0.1 moles) was added in about 10 minutes. Rapid stirring was continued for 10 minutes after the addition was complete, stirring was discontinued, and the mixture was allowed to stand for 10 minutes to separate to a dark red organic phase and a clear colorless water phase. The organic phase weighed 87 g and contained 25% manganese neodecanoate, which after removing the solvent by evaporation was a dark red viscous liquid with viscosity>200,000 cps.

EXAMPLE 17

To demonstrate the removal of hydrogen sulfide odors from metal working fluids, the following test was run.

10 g of a sulfated oil based soluble oil was mixed with 190 g of water and 0.08 g of sodium sulfide nonahydrate was dissolved in the mixture. The mixture was divided into two equal portions, and 0.10 g of zinc neodecanoate (Example 1) was added to one portion and thoroughly dispersed. 0.3 ml of 1 N HCl was added to each portion and mixed to release hydrogen sulfide, and the samples were capped. The vapor phase over the two samples was tested for the presence of hydrogen sulfide using lead acetate test strips. The vapor above the sample without zinc neodecanoate contained hydrogen sulfide as evidenced by the brown coloration of the test strip. Hydrogen sulfide was absent in the vapor above the sample with zinc neodecanoate and the test strip did not change color.

EXAMPLE 18

To demonstrate the efficacy of the compositions of this invention in removing odor producing $H_2S$ from hydrocarbon oil, $H_2S$ was generated at a concentration of 435 ppm in 100 second paraffinic oil and the compositions of this invention were used to remove the $H_2S$.

The tests were performed as follows.

1 ml of 10% sodium sulfide was added to 100 g of the oil in a separatory funnel and shaken thoroughly to mix. 0.2 g of acetic acid were added and the contents of the funnel were shaken again to generate hydrogen sulfide in the oil.

10 g portions of this mixture were added to test tubes containing the metal salts and quantities noted in Table 1, and thoroughly mixed. The headspace in the test tubes was exposed to lead acetate test paper to detect $H_2S$. The period of time in minutes necessary to reduce $H_2S$ levels to below that detectable by this method is noted in the table.

TABLE 1

| Scavenger composition | quantity, g | time required to eliminate $H_2S$ |
|---|---|---|
| Zinc neodecanoate Example 2(a) | 0.10 | <2 minutes |
| Zinc neodecanoate, Example 2(c) | 0.052 | 15 minutes |
| | 0.104 | <2 minutes |

TABLE 1-continued

| Scavenger composition | quantity, g | time required to eliminate H₂S |
|---|---|---|
| Zinc naphthenate | 0.09 | 12 minutes |
| Example 10, not diluted | 0.143 | 8 minutes |
| Copper neodecanoate Example 13 | 0.053 | <2 minutes |
| Nickel neodecanoate Example 14 | 0.051 | 19 minutes |
|  | 0.102 | 19 minutes |
| Iron neodecanoate Example 15 | 0.053 | 24 minutes |
|  | 0.11 | 23 minutes |
| Manganese neodecanoate Example 16 | 0.20 | 5 minutes |

EXAMPLE 19

To demonstrate the removal of H₂S odors from air, the composition of Example 2(a) was absorbed onto precipitated silica at a ratio of 7 parts of zinc neodecanoate to 3 parts of silica to form a free flowing powder. 1 g of this powder was spread on a watch glass. 4.4 g of a 1% solution of Na₂S.9H₂O was placed in a 1 l beaker, 0.3 ml of 1 N HCl was added to generate H₂S, the watch glass with the powdered product was placed in the beaker, and the beaker was sealed. At periodic intervals the head space was sampled for the presence of H₂S with lead acetate test paper. After 1 hour the H₂S had disappeared from the head space; a blank without the scavenger composition still gave a positive test after 24 hours.

The invention can be embodied in other forms without departing from the spirit or essential attributes thereof Particularly it will be appreciated by those skilled in the art that there are many other conditions wherein it would be desirable to control odors from sulfhydryl compounds other than those demonstrated herein. Reference should therefore be had to the following claims, rather than to the foregoing'specification to determine the scope of the invention.

I claim:

1. A composition comprising
   a. hydrocarbon oil soluble metal carboxylates chosen from the group consisting of

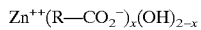
   $$Zn^{++}(R{-}CO_2^-)_x(OH)_{2-x}$$

wherein x is 1 or 2, and R a hydrocarbyl radical containing from about 4 to about 19 carbon atoms and mixtures of said oil soluble metal carboxylates, and
   b. sulfhydryl compounds.

2. The composition of claim 1 wherein the said metal carboxylates are liquid at about 25° C.

3. The composition of claim 2 wherein the carboxylic acid is chosen from the group consisting of neoacids, naphthenic acids, isoacids, and Guerbet acids, and mixtures of said acids.

4. The composition of claim 3 wherein the carboxylic acid is neodecanoic acid.

5. The composition of claim 2 wherein the carboxylic acid is chosen from the group consisting of neoacids and mixtures of neoacids.

6. The composition of claim 2 wherein the carboxylic acid is chosen from the group consisting of naphthenic acids and mixtures of naphthenic acids.

7. The composition of claim 1 wherein the carboxylic acid is chosen from the group consisting of neoacids, naphthenic acids, isoacids, and Guerbet acids, and mixtures of said acids.

8. The composition of claim 1 wherein the carboxylic acid is chosen from the group consisting of neoacids and mixtures of neoacids.

9. The composition of claim 1 wherein the carboxylic acid is chosen from the group consisting of naphthenic acids and mixtures of naphthenic acids.

10. The composition of claim 1 wherein the carboxylic acid is chosen from the group consisting of Guerbet acids and mixtures of Guerbet acids.

11. The composition of claim 1 wherein the carboxylic acid is chosen from the group consisting of isoacid and mixtapes of isoacids.

12. The composition of claim 1 wherein the quantity of metal carboxylate (a) is sufficient to react with substantially all of the sulfhydryl compounds (b).

13. A method for controlling odors produced by sulfhydryl compounds wherein the compositions containing the said sulfhydryl compounds are contacted with metal carboxylates chosen from the group consisting of

$$Zn^{++}(R{-}CO_2^-)_x(OH)_{2-x}$$

wherein x is 1 or 2, and R a hydrocarbyl radical containing from about 4 to about 19 carbon atoms and mixtures of said compositions.

* * * * *